United States Patent [19]

Nakanishi et al.

[11] 4,341,868
[45] Jul. 27, 1982

[54] METHOD AND TEST COMPOSITION FOR THE DETERMINATION OF THE SUBSTRATE FOR XANTHINE OXIDASE

[75] Inventors: Toru Nakanishi, Atsugi; Yozo Machida, Machida, both of Japan

[73] Assignee: Kyowa Hakko Kogyo Co., Ltd., Tokyo, Japan

[21] Appl. No.: 201,067

[22] Filed: Apr. 18, 1980

[30] Foreign Application Priority Data

Aug. 18, 1978 [JP] Japan ............................... 53-100784
Feb. 10, 1979 [JP] Japan ................................ 54-13828
Aug. 17, 1979 [WO] PCT Int'l Appl. ... PCT/JP79/00219

[51] Int. Cl.$^3$ ........................... C12N 9/06; C12Q 1/26; C12R 1/01
[52] U.S. Cl. ................................................. 435/191
[58] Field of Search ................... 435/25, 28, 189, 191, 435/822; 424/2, 7

[56] References Cited

U.S. PATENT DOCUMENTS 3,099,605  7/1963  Free ........................................ 435/8
4,105,800  8/1978  Jahns et al. ............................ 426/61
4,246,341  1/1981  Zikakis ................................... 435/25

FOREIGN PATENT DOCUMENTS 2359850  6/1978  France .

OTHER PUBLICATIONS

Hashimoto, "A New Spectrophotometric Assay Method of Xanthine Oxidase in Crude Tissue Homogenate", *Anal. Biochem.*, vol. 62, No. 2, (1974), pp. 426–435.
Fried et al., "Xanthine Oxidase", (Xanthine Dehydrogenase), *Methods of Enzymatic Analysis*, Bergmeyer ed., Academic Press, N.Y., (1974), pp. 644–649.
Fried et al., "Hypoxanthine and Xanthine Colorimetric Assay", *Methods of Enzymatic Analysis*, Bergmeyer, ed., Academic Press, N.Y., (1974), pp. 1941–1945.
Nakanishi et al., "Fermentative Production of Uricase", *Chem. Abstracts*, vol. 90, No. 23, p. 500, (1979) Absts. No. 184922g.
Jorgensen, "Hypoxanthime and Xanthine UV-Assay", *Methods of Enzymatic Analysis*, Bergmeyer, ed. Academic Press., N.Y. (1974), pp. 1941–1945.
Bergmeyer H. U.: "Methoden der Enzymatischen Analyse", vol. 1, 1974, pp. 682–688, vol. 2, 1974, pp. 1957–1963, 1976–1982, 1988–1998.

*Primary Examiner*—Thomas G. Wiseman
*Attorney, Agent, or Firm*—Fitzpatrick, Cella, Harper & Scinto

[57] ABSTRACT

The substrate for xanthine oxidase such as xanthine, hypoxanthine, guanine, 2-hydroxypurine, etc. are determined by oxidizing the substrate by the action of xanthine oxidase derived from a microorganism and determining the formed hydrogen peroxide by the system for the determination of hydrogen peroxide comprising peroxidase and coloring reagent.

The determination is carried out in one step by using the test composition for the determination of the substrate for xanthine oxidase which comprises xanthine oxidase and a system for the determination of hydrogen peroxide.

The determination method can be applied to the determination of the compound which participates in the system wherein the substrate is stoichiometrically formed by the reaction or decomposition. When the system is an enzymatic reaction, the compound is determined in one step.

Xanthine oxidase used in the present invention is different from known xanthine oxidase in molecular weight and is prepared by culturing a microorganism belonging to the genus Enterobacter.

17 Claims, 9 Drawing Figures

METHOD AND TEST COMPOSITION FOR THE DETERMINATION OF THE SUBSTRATE FOR XANTHINE OXIDASE

TECHNICAL FIELD

The present invention relates to a method for the determination of the substrate for xanthine oxidase in a sample using xanthine oxidase derived from a microorganism and a test composition suitable therefor.

The present invention also pertains to a method for the determination of a reactant in the reaction system wherein the substrate for xanthine oxidase is quantitatively formed by the reaction or decomposition and the determination of the activity of enzyme which catalyzes the reaction in the system, and a test composition used therefor.

The present invention further pertains to a novel xanthine oxidase suitable for the determination described above and a process for producing the enzyme using a microorganism.

BACKGROUND ART

It is known that xanthine oxidase (EC 1.2.3.2) catalyzes the oxidation of the substrate thereof such as hypoxanthine to form uric acid and hydrogen peroxide and that the enzyme exists in milk. The enzyme derived from milk is available.

The determination of the substrate for an oxidase by oxidizing the substrate by the action of the oxidase and determining the amount of reaction product stoichiometrically formed is generally conducted. For example, it has been known that hypoxanthine is oxidized by the action of xanthine oxidase to form uric acid and hydrogen peroxide. Therefore, it is easily understood that the determination of the substrate can be performed by determining the amount of formed uric acid or hydrogen peroxide.

When the substrate is determined from the amount of a product obtained by oxidizing the substrate by the action of oxidase, the determination is generally carried out by reacting the formed hydrogen peroxide with a coloring reagent and determining the amount of the formed hydrogen peroxide by measuring the absorbancy of the reaction solution in visible ray region.

When the substrate is oxidized by the action of xanthine oxidase derived from milk and the formed hydrogen peroxide is introduced into a pigment system, the formed pigment is unstable and is decomposed in a brief period of time. Therefore, the substrate cannot be determined by the change in absorbancy in visible ray region. Accordingly, the substrate is generally determined by the change in absorbancy in ultraviolet region based on the formation of uric acid without the determination of hydrogen peroxide.

After studying the process for producing a xantine oxidase by fermentation, the present inventors have found that xanthine oxidase is produced by culturing a microorganism belonging to the genus Enterobacter and capable of producing xanthine oxidase in a nutrient medium.

It has been found that when the substrate is oxidized by the action of xanthine oxidase derived from microorganism and the formed hydrogen peroxide is introduced into a pigment system, the formed pigment is stable and the substrate in a sample can be determined by measuring the absorbancy in visible ray region based on the pigment.

It has been known that the enzyme derived from microorganism belonging to the genus Pseudomonas, Escherichia, Arthrobacter, Nocardia or the like exhibits a weak activity of xanthine oxidase. [J. Bacteriology, 130, 1175 (1977)]. However, these enzymes do not have a sufficiently strong activity for the determination of the substrate.

DISCLOSURE OF INVENTION

According to the present invention, the substrate for xanthine oxidase is determined by oxidizing the substrate by the action of xanthine oxidase derived from microorganism in an appropriate buffer solution, introducing the formed hydrogen peroxide into a pigment system and measuring the absorbancy in visible ray region based on the formed pigment.

The present invention is based on the following principle. When the substrate for xanthine oxidase, that is, xanthine, hypoxanthine, guanine or 2-hydroxypurine is oxidized by the action of xanthine oxidase, the amount of the formed hydrogen peroxide is directly proportional to the amount of the substrate in a sample. The formed hydrogen peroxide is determined by reacting the hydrogen peroxide with coloring reagent in the presence of peroxidase and measuring the absorbancy of the reaction solution by the formation of pigment at 400~600 nm.

The present invention can be applied to the determination of the compound which participates in the reaction system wherein the substrate for xanthine oxidase is quantitatively formed by the reaction or decomposition and the determination of the activity of enzyme which catalyzes the reaction in the system.

Examples of the compound which can be determined by the present invention include purine base derivatives such as inosine, xanthosine, guanosine, adenosine and deoxyinosine and inorganic phosphoric acid. The purine base derivatives are decomposed with an acid or an enzyme and the formed hypoxanthine, xanthine, guanine, etc. may be determined according to the method of the present invention.

As the enzyme which catalyzes the conversion of the purine base derivative into the substrate for xanthine oxidase, nucleosidase, purine nucleoside phosporylase, adenosine deaminase and nucleosidase, and adenosine deaminase and purine nucleoside phosphorylase are exemplified.

For example, inosine reacts with inorganic phosphoric acid in the presence of purine nucleoside phosphorylase to form hypoxanthine and ribose-1-phosphate. Inosine is converted by the action of nucleosidase to hypoxanthine and ribose. Adenosine is converted by the action of adenosine deaminase and purine nucleoside phosphorylase to hypoxanthine and ribose-1-phosphate through inosine.

These reactions proceed stoichiometrically to form xanthine or hypoxanthine. The determination of starting compounds or activity of enzyme used in the reaction may be performed by determining the formed xanthine or hypoxanthine according to the method of the present invention.

The determination of inorganic phosphoric acid may be performed by reacting the inorganic phosphoric acid with purine base such as inosine, deoxyinosine and the like in the presence of purine nucleoside phosphorylase to form hypoxanthine and determining the hypoxanthine according to the method of the present invention.

The present invention also pertains to a test composition (I) useful for the determination of the substrate for xanthine oxidase. Said composition comprises xanthine oxidase derived from a microorganism, peroxidase and a coloring reagent.

The present invention relates to a test composition (II) useful for the determination of purine base derivatives or inorganic phosphoric acid. Said composition comprises the enzyme for converting the purine base derivatives to the substrate for xanthine oxidase and a system for determining the substrate for xanthine oxidase.

In the determination of the substrate for xanthine oxidase, the sample containing the substrate and xanthine oxidase are added to buffer solution having a pH of 6.5~8 and the mixture is subjected to reaction. Xanthine oxidase can be used as a microcapsule or an immobilized enzyme, if necessary.

As a buffer solution, tris-hydrochloride buffer, borate buffer and the like may be used. The amount of the enzyme used in the reaction is usually 0.5~10 U per 0.1~2.5 μmol of the substrate and the reaction is carried out after the mixture is made up to 3 ml with water.

The formed hydrogen peroxide may be introduced into a pigment system by any known methods. For example, peroxidase and a coloring reagent are used for the formation of a pigment.

Examples of coloring reagent include 4-aminoantipyrine and phenol, 4-aminoantipyrine and dimethylaniline, 3-methyl-2-thiazolinone hydrazone (hereinafter referred to as MBTH) and O-toluidine, MBTH and N,N-dimethylaniline, O-dianisidine and 4,4′,4″-methylidyne-tris.

The reaction is carried out using 2~10 U of peroxidase and 5~20 μmol of coloring reagent per 3 ml of the solution. The enzymatic reaction is carried out at 30°~40° C. for about 10~20 minutes. The absorbancy of the reaction solution by the formation of pigment is measured in visible ray region, usually at 400~600 nm.

The standard curve showing the relation between the amount of the substrate and absorbancy is prepared in advance on the authentic compound and the content of the substrate in a sample can be obtained from the absorbancy.

In the present method, the process for oxidizing the substrate and the process for introducing the thus formed hydrogen peroxide into a pigment system may be carried out individually. Preferably, xanthine oxidase, and a test composition for the determination of hydrogen peroxide comprising peroxidase and coloring reagent are added to the sample and the reaction is carried out in one step to obtain a colored reaction solution. Then the determination is simply performed by measuring the absorbancy of the reaction solution in visible ray region.

In the determination of purine base derivatives or phosphoric acid, these compounds are converted to the substrate for xanthine oxidase and the substrate is determined according to the method for the determination of xanthine described above.

The determination may be performed by conducting the reaction to form the substrate for xanthine oxidase and the determination of the substrate stepwise, and may preferably performed in one step by adding an enzyme for converting the compound to be determined to the substrate for xanthine oxidase, xanthine oxidase and coloring reagent and optionally a compound which participates in the reaction to the sample for conducting the reaction.

The test composition (I) or (II) useful for the determination in one step is explained in detail below. The test composition (I) comprises 0.5~1.0 U of xanthine oxidase, 2~10 U of peroxidase and 5~20 μmol of coloring reagent. The kit consisting of the components of the composition combined according to the purposes is convenient for practical use. 1~5 ml of buffer solution may be added to the kit.

The test composition (II) of the present invention comprises the test composition (I) and a system for producing the substrate for xanthine oxidase.

Examples of said system are (1) purine base and purine nucleoside phosphorylase for the determination of inorganic phosphoric acid, (2) nucleosidase for the determination of inosine and (3) adenosine deaminase and purine nucleoside phosphorylase for the determination of adenosine. The components of the composition (II) may also be combined to make a kit for practical use.

The xanthine oxidase used in the determination method and test composition of the present invention is a novel enzyme which is distinguished from known xanthine oxidase. Said enzyme is obtained by culturing a microorganism belonging to the genus Enterobacter and capable of producing xanthine oxidase in a nutrient medium and recovering the same from the culture liquor. The enzyme differs from known ones in some properties.

The properties of the present enzyme are as follows. The enzyme activity is measured by the following two methods.

Method I

In this method, 1.6 ml of water is added to the mixture of 1.0 ml of 0.1 M tris-hydrochloride buffer (pH 7.3), 0.2 ml of 10 mM xanthine aqueous solution and 0.2 ml of xanthine oxidase solution to make up 3 ml solution. The reaction is carried out at 37° C. for ten minutes. After completion of the reaction, 12 ml of 0.2 N hydrochloric acid is added to the reaction mixture and the absorbancy of the reaction solution is measured at 283 nm. The thus obtained value is defined as $OD_{283}$. This value corresponds to the amount of uric acid formed.

Separately, the enzyme solution containing the same components as described above is heated to 37° C. and then 12 ml of 0.2 N hydrochloric acid is added thereto. The resultant solution is used as a blank.

Since the reaction product, uric acid has a maximum absorption at 283 nm in acidic region and the molecular extinction coefficient is $1.238 \times 10^4$ (Analytical Biochemistry 38, 65, 1970), the unit (U) of xanthine oxidase is as follows:

$$OD_{283} \times 0.606 \times \text{Dilution ratio of enzyme}$$

One unit of enzyme activity is defined as the activity of enzyme which forms 1 μmol of uric acid in one minute at 37° C. and at a pH of 7.3.

Method II

In this method, 3.0 ml of enzyme solution comprising 1.0 ml of 0.1 M tris-hydrochloride buffer (pH 7.3), 0.5 ml of coloring solution, 0.2 ml of 10 mM xanthine aqueous solution, 0.2 ml of xanthine oxidase solution and 1.1 ml of water is incubated at 37° C. for 10 minutes. The coloring solution is prepared by adding 445 U/100 ml peroxidase to 0.1 M tris-hydrochloride buffer (pH 7.3) containing 10 mmol/l 4-aminoantipyrine and 10 mmol/l phenol.

After completion of the reaction, the absorbancy of the reaction solution is measured at 500 nm. Molecular extinction coefficient of quinoneimine pigment formed in the reaction is $5.33 \times 10^3$ (Clinical Chemistry 20, 470, 1974). When a unit of enzyme activity is defined as the activity of enzyme which forms 1 μmol of hydrogen peroxide in one minute at 37° C. and at a pH of 7.3, the unit (U) of xanthine oxidase is as follows:

$OD_{500} \times 0.563 \times$ Dilution ratio of enzyme

Xanthine oxidase of the present invention has the following enzymological properties.

(1) Action

The enzyme catalyzes the oxidation of hypoxanthine in the presence of oxygen as the acceptor to form stoichiometrically xanthine and hydrogen peroxide, and catalyzes the oxidation of xanthine in the presence of oxygen as an acceptor to form stoichiometrically uric acid and hydrogen peroxide.

Hypoxanthine + $O_2$ + $H_2O$ → Xanthine + $H_2O_2$

Figures 1, 2:
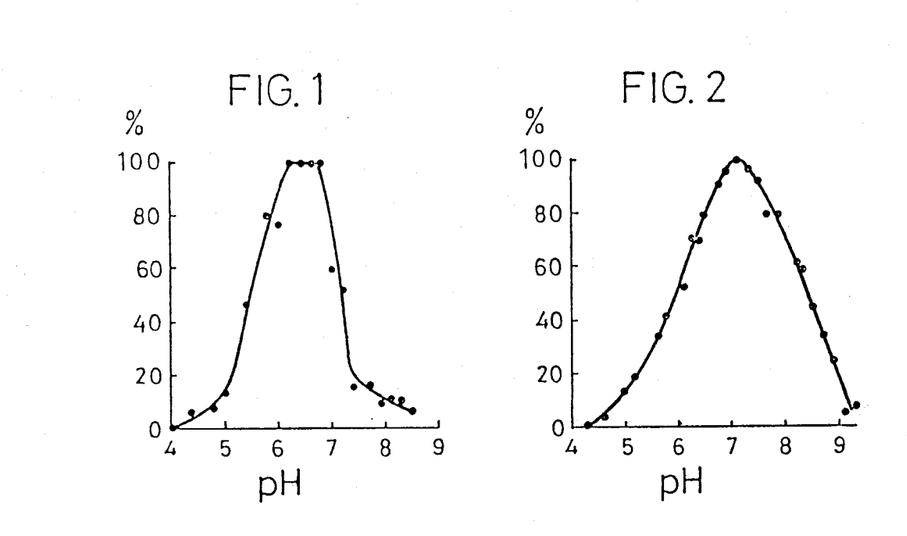
FIG. 1: Stable pH range
FIG. 2: Optimum pH range

Xanthine + $O_2$ + $H_2O$ → Uric acid + $H_2O_2$ (2) Stable pH range 0.2 M acetate buffer and 50 mM borate buffer are mixed to make solutions having various pH values (4.0, 4.4, 4.8, 5.0, 5.4, 5.8, 6.0, 6.2, 6.4, 6.6, 6.8, 7.0, 7.2, 7.4, 7.7, 7.9, 8.1, 8.3 and 8.5). The enzyme preparate is dissolved in the solution to make an enzyme solution having an enzyme activity of 49 mU/ml. Then the solution is incubated at 60° C. for 30 minutes. After cooling, xanthine oxidase activity of the resultant solution is determined according to Method I. The results are shown in FIG. 1. FIG. 1 shows that the stable pH range of the present xanthine oxidase is 6.2~6.8.

(3) Optimum pH 0.2 M acetate buffer and 50 mM borate buffer are mixed to make 2 ml of solutions having various pH values (4.3, 4.6, 5.0, 5.2, 5.6, 5.8, 6.1, 6.3, 6.4, 6.5, 6.8, 6.9, 7.1, 7.3, 7.5, 7.7, 7.9, 8.1, 8.3, 8.5, 8.7, 8.9, 9.1 and 9.3). To the solution is added 0.2 ml of 0.25 U/ml xanthine oxidase solution.

The enzymatic reaction is carried out using xanthine as a substrate. After the reaction is terminated by the addition of 0.2 N hydrochloric acid, the absorbancy of the reaction solution is measured at 283 nm. The results are shown in FIG. 2, from which the optimum pH of the present xanthine oxidase is found to be around 7.1.

Figure 3:
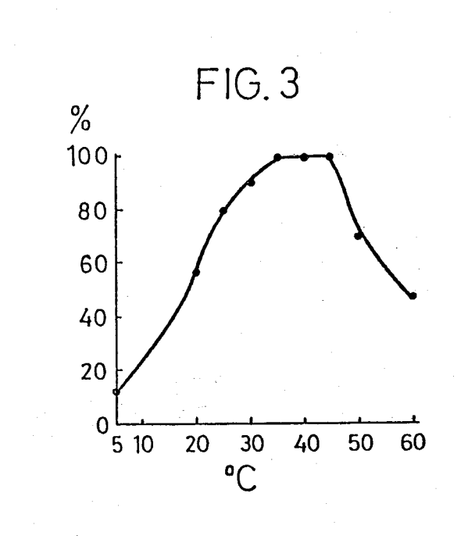
FIG. 3: Optimum temperature

(4) Optimum temperature 0.2 ml of 0.25 U/ml enzyme solution is added to 2.0 ml of 50 mM borate buffer (pH 7.0). The reaction is carried out at various temperatures (5°, 20°, 25°, 30°, 35°, 40°, 45°, 50° and 60° C.) for 10 minutes using xanthine as a substrate. After the reaction is terminated by the addition of 0.2 N hydrochloric acid, the absorbancy of the reaction solution is measured at 283 nm. The results are shown in FIG. 3, from which the optimum temperature is found to be 35°~45° C.

(5) Substrate specificity

The same procedures as in Method II are repeated except that 0.25 U/ml xanthine oxidase and 0.1 ml of 5 mM solutions of various substrates are used, and the amount of the formed hydrogen peroxide is determined.

Table 1 shows the relative activity on several substrates, the activity on xanthine being defined as 100.

TABLE 1

| Substrate | Relative activity (%) |
|---|---|
| Xanthine | 100 |
| Hypoxanthine | 92.3 |
| Guanine | 53.3 |
| Adenine | 0 |
| Purine | 23.3 |
| 2-Hydroxypurine | 88.5 |
| Guanosine | 0 |
| Adenosine | 2.5 |
| Xanthosine | 0 |
| Inosine | 0 |
| Uric acid | 0 |
| Theophylline | 0 |
| Theobromine | 0 |
| 6-mercaptopurine | 4.4 |
| NADH | 0 |

As apparent from Table 1, the present xanthine oxidase exhibits a strong activity on xanthine, hypoxanthine, guanine, purine and 2-hydroxypurine.

(6) Heat stability 0.5 mg of 0.25 U/ml xanthine oxidase solution is added to 2.0 ml of 50 mM borate buffer (pH 6.6). The mixture is incubated at 5°, 30°, 35°, 40°, 45°, 50°, 60°, 70° or 80° C. for 30 minutes and then cooled with ice for 5 minutes. The activity of the solution is determined according to Method I.

Figure 4:
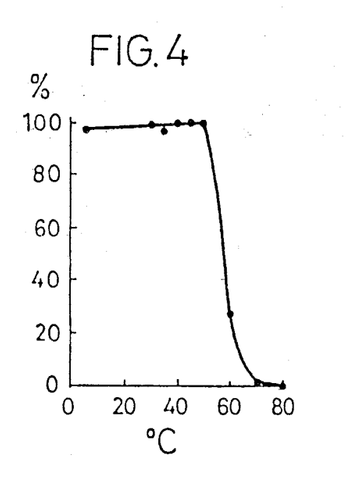
FIG. 4: Heat stability

The results are shown in FIG. 4. As can be seen from FIG. 4, the present xanthine oxidase has 100% activity after the treatment at 50° C. for 30 minutes based on that before the treatment.

(7) Inhibitor

Xanthine oxidase activity is determined in the same manner as in Method I except that 0.25 U/ml xanthine oxidase solution is used and various enzyme inhibitors are added. The results are shown in Table 2.

TABLE 2

| Compound | Concentration of inhibitor (M) | Inhibition rate (%) |
|---|---|---|
| CuCl | $1 \times 10^{-4}$ | 90.5 |
|  | $1 \times 10^{-5}$ | 53.5 |
|  | $1 \times 10^{-6}$ | 2.2 |
| $CuCl_2.2H_2O$ | $1 \times 10^{-4}$ | 96.3 |
|  | $1 \times 10^{-5}$ | 79.6 |
|  | $1 \times 10^{-6}$ | 12.9 |
|  | $1 \times 10^{-7}$ | 0 |
| $AgNO_3$ | $1 \times 10^{-4}$ | 97.8 |
|  | $1 \times 10^{-5}$ | 98.2 |
|  | $1 \times 10^{-6}$ | 54.8 |
|  | $1 \times 10^{-7}$ | 0 |
| $FeSO_4.7H_2O$ | $1 \times 10^{-4}$ | 92.3 |
|  | $1 \times 10^{-5}$ | 0 |
| PCMB* | $1 \times 10^{-4}$ | 76.6 |
|  | $1 \times 10^{-5}$ | 34.7 |
|  | $1 \times 10^{-6}$ | 0 |
| L-ascorbic acid | $1 \times 10^{-3}$ | 88.9 |
|  | $1 \times 10^{-4}$ | 82.7 |
|  | $1 \times 10^{-5}$ | 61.7 |
|  | $1 \times 10^{-6}$ | 0 |

*: Sodium salt of p-chloromercuribenzoic acid

As can be seen from Table 2, CuCl, $CuCl_2.2H_2O$, $AgNO_3$, $FeSO_4.7H_2O$, PCMB, and L-ascorbic acid are inhibitors of xanthine oxidase.

(8) Molecular weight

The molecular weight of the enzyme determined by gel filtration method using Sephadex G-200 is 128,000.

(9) Isoelectric point 3.8 (Determined by electrophoresis using carrier ampholyte).

(10) Experiment of enzyme action

The following experiment shows the quantitative formation of hydrogen peroxide by the oxidation of xanthine or hypoxanthine by the action of the enzyme.

EXPERIMENT 1

As a coloring solution, 0.1 M tris-hydrochloride buffer (pH 7.3) containing 10 mmol/l 4-aminoantipyrine, 10 mmol/l phenol and 490 U/100 ml peroxidase is prepared. 3 ml of a mixture containing 0.5 ml of the coloring solution, 1.0 ml of 0.1 M tris-hydrochloride buffer (pH 7.3), 0.93 U of xanthine oxidase obtained in the example described later and xanthine or hypoxanthine at a concentration indicated in the table below is subjected to reaction at 37° C. for 20 minutes. The absorbancy of the reaction solution is measured at 500 nm. The amount formed of hydrogen peroxide calculated from calibration curve is shown in the table. As can be seen from the results, hydrogen peroxide is formed quantitatively.

| Substrate | Concentration of substrate [A] | Amount of formed hydrogen peroxide [B] | [B]/[A] |
|---|---|---|---|
| Hypoxanthine | 0.15 μmol | 0.27 μmol | 1.80 |
| Xanthine | 0.15 μmol | 0.14 μmol | 0.93 |

(11) Stability in introduction of the hydrogen peroxide formed by the enzymatic reaction into a pigment system Hypoxanthine is oxidized by the action of the present enzyme and the formed hydrogen peroxide is reacted with a coloring reagent. The following experiment shows that the formed pigment is more stable than that formed using xanthine oxidase derived from milk.

EXPERIMENT 2

A mixture of 1.0 ml of 0.1 M tris-hydrochloride buffer (pH 7.3), 0.1 ml of 10 mM hypoxanthine solution, 0.5 ml of coloring solution of Experiment 1 and xanthine oxidase is made up to 3.0 ml with water. 0.4 mg xanthine oxidase derived from milk (product of Boehringer Mannheim Co.) or 0.15 U of the xanthine oxidase obtained in Example 1 is used per 3.0 ml of solution.

The enzyme-containing solution is subjected to reaction at 37° C. and the absorbancy of the reaction solution colored by the formation of quinoneimine derived from hydrogen peroxide is measured at 500 nm at regular intervals.

Figure 5:
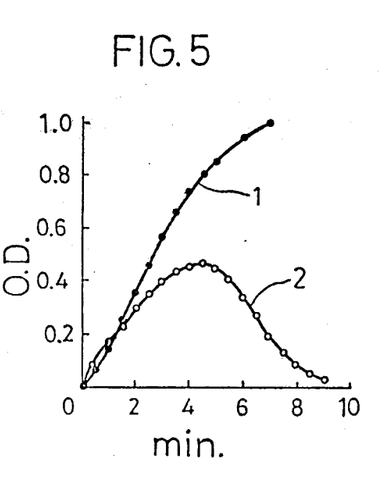
FIGS. 5 and 6: The change in optical density (OD) with time by the formation of uric acid (1) and the formation of pigment based on the formed hydrogen peroxide in the enzymatic reaction using the present xanthine oxidase (FIG. 6) and the xanthine oxidase derived from milk (FIG. 5). The ordinate shows OD value and the abscissa shows reaction time (minute).
Figure 6:
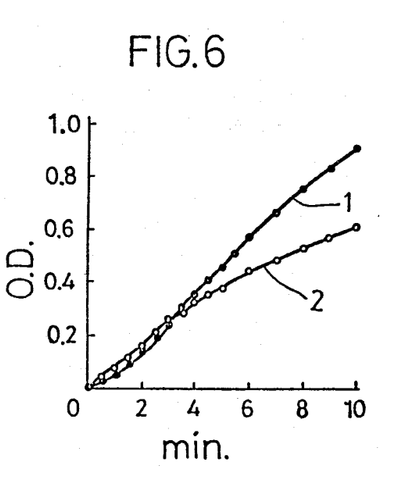

On the other hand, for the determination of uric acid formed in the reaction, a mixture of 1.0 ml of 0.1 M tris-hydrochloride buffer (pH 7.3), 0.1 ml of 10 mM hypoxanthine aqueous solution and the same amount of xanthine oxidase as described in the determination of hydrogen peroxide is made up to 3.0 ml with water. The solution is subjected to reaction at 37° C. and the absorbancy of the reaction solution is measured at 293 nm at regular intervals. The results are shown in FIGS. 5 and 6. When xanthine oxidase derived from milk is used, the amount of a pigment reaches maximum 4 minutes and a half after the start of reaction and then decrease in spite of the continuous formation of uric acid (FIG. 5).

On the other hand, such a phenomenon is not observed when the present enzyme is used. That is, the formation of pigment parallels that of uric acid and loss of pigment is not observed.

(12) Acceptor of the present enzyme

The following experiment shows that oxygen is the best acceptor of the present enzyme.

EXPERIMENT 3

0.15 ml of 10 mM xanthine aqueous solution, 1.0 ml of 100 mM tris-hydrochloride buffer (pH 7.3), 0.65 ml of water and 1 ml of various electron acceptors shown in Table 3 are mixed. The mixture and a solution of xanthine oxidase obtained in Example 1 are incubated at 37° C. and then nitrogen gas is introduced into the mixture and the enzyme solution for 3~4 minutes to remove dissolved oxygen.

Then, 0.2 ml of 0.25 U/ml xanthine oxidase is added to 2.8 ml of the reaction mixture to initiate the reaction and the absorbancy is measured every 15 seconds. The values obtained during one minutes of 30 to 90 seconds after the addition of xanthine oxidase is used as data.

When oxygen is used as an acceptor, nitrogen gas is not introduced into the mixture and the reaction product, uric acid obtained using dissolved oxygen is determined by measuring the absorbancy at 295 nm.

The results are shown in Table 3.

TABLE 3

| Electron acceptor | Concentration of acceptor (mM) | Wave length (nm) | Relative activity (%) |
|---|---|---|---|
| Oxygen | Dissolved oxygen | 295 | 100 |
| DCPIP* | 0.04 | 600 | 9.2 |
| Potassium ferricyanide | 0.5 | 420 | 6.0 |
| Cytochrome C | 0.1 | 550 | 0 |
| NAD | 0.1 | 340 | 0 |
| NADP | 0.1 | 340 | 0 |

*2,6-sodium salt of dichlorphenol indophenol

When xanthine oxidase derived from milk is used, the relative activity is 100 for ferricyanide, 83 for oxygen, 35 for indophenol, and <1.3 for NAD (The Enzymes' Third edition Vol. XII Oxidation—Reduction Part B, p.299, 1975 Academic Press). There is a great difference in relative activity between the present xanthine oxidase and the enzyme derived from milk when ferricyanide or indophenol is used.

The process for producing the enzyme of the present invention is explained in detail below.

As a microorganism used in the present invention, any microorganism belonging to the genus Enterobacter and capable of producing xanthine oxidase may be used. An example of preferred strain is *Enterobacter cloacae* KY 3066. The strain has been deposited with the Institute for Microbial Industry and Technology, Chiba-ken, Japan under FERM P 4077. The strain has also been deposited with Northern Regional Research Laboratory at Peoria, Illinois 61604, U.S.A. and has been accorded accession number NRRL B-11155. The microbiological properties of *Enterobacter cloacae* are disclosed in Bergey's Manual of Determinative Bacteriology 8th edition, page 325.

Either a synthetic or natural medium may be used as long as it contains an appropriate carbon source, nitrogen source, inorganic materials and other nutrients necessary for the particular strain.

As carbon sources, carbohydrates such as glucose, fructose, sucrose, molasses, etc., nucleic acids such as xanthine, hypoxanthine, guanine, purine, inosine, guanosine, xanthosine disodium 5'-inosinate, disodium 5-guaninate, etc. and the like may be used.

As nitrogen sources, inorganic and organic nitrogen compounds, for example, ammonium salts such as ammonium chloride, ammonium sulfate, ammonium phosphate, etc., nucleic acids such as xanthine, hypoxanthine, guanine, purine, inosine, guanosine, xanthosine, disodium 5'-inosinate, disodium 5'-guaninate, etc., amino acids such as glutamic acid, etc., natural nitrogenous materials such as peptone, meat extract, yeast extract, corn steep liquor, etc. and the like may be used.

As inorganic materials, potassium dihydrogen phosphate, dipotassium monohydrogen phosphate, magnesium sulfate, and the like may be used.

In the present invention, the yield of xanthine oxidase can be enhanced by the addition of xanthine oxidase inducer, for example nucleic acids such as xanthine, hypoxanthine, guanine, guanosine, inosine, disodium 5'-inosinate, disodium 5'-guaninate, etc. and the like as shown in Experiment 4 hereinafter. The preferable concentration of nucleic acids in a medium is 0.2~3.0 g/dl.

Culturing is generally carried out with shaking or with aeration and agitation. Culturing is carried out at a temperature of 20°~35° C., preferably 25°~30° C., and at a pH of 6.0~9.5, preferably 6.5~9.0 and is completed in 1~3 days, generally 1~2 days.

Xanthine oxidase is accumulated in culture broth, expecially in microbial cells by the cultivation described above. Recovery of xanthine oxidase from culture broth is carried out as follows.

After completion of the culturing, culture liquor is subjected to centrifugation, etc. to obtain microbial cells. The microbial cells are disrupted by appropriate means and the disrupted cell suspension is subjected to centrifugation, etc. to obtain a supernatant. Then the supernatant is subjected to conventional purification methods such as salting-out, precipitation using organic solvent, dialysis, column chromatography using ion exchange cellulose, Sephadex, ion exchange Sephadex, etc., freeze-drying and the like to obtain the purified xanthine oxidase.

The following experiment shows that the yield of xanthine oxidase is enhanced by the addition of nucleic acid to the medium.

EXPERIMENT 4

In this experiment, 40 ml of medium (pH 7.2) comprising hypoxanthine having concentrations indicated in Table 4, 0.5 g/dl yeast extract, 0.5 g/dl corn steep liquor, 0.1 g/dl peptone, 0.05 g/dl $KH_2PO_4$, 0.1 g/dl $K_2HPO_4$ and 0.05 g/dl $MgSO_4.7H_2O$ is poured into Sakaguchi flask and is sterilized at 120° C. for 15 minutes.

One loopful of the seed culture of *Enterobacter cloacae* KY 3066, FERM P 4077, NRRL B-11155 in a slant is inoculated into the medium and culturing is carried out with shaking at 30° C. for 48 hours.

After completion of the culturing, the culture liquor is subjected to centrifugation at 10,000 r.p.m for 15 minutes (hereinafter centrifugation is carried out under this condition) to obtain microbial cells. The thus obtained cells are suspended in 20 ml of 50 mM tris-hydrochloride buffer (pH 8.0) and then disrupted for ten minutes in an ultrasonic disintegration (Ultrasonic Generator KMS-250 type, made by Kubota Seisaku-sho). The resulting disrupted cell suspension is centrifuged to obtain a supernatant. Xanthine oxidase activity of the supernatant is determined according to the Determination Method II and the results are shown in Table 4 below.

TABLE 4

| Hypoxanthine concentration (g/dl) | Xanthine oxidase activity (U/dl) |
|---|---|
| 0 | 6.5 |
| 0.1 | 20.0 |
| 0.2 | 31.2 |
| 0.3 | 47.3 |
| 0.5 | 48.4 |
| 1.0 | 55.2 |
| 3.0 | 49.0 |

As can be seen from Table 4, the preferable concentration of hypoxanthine as an inducer of xanthine oxidase in the medium is more than 0.2 g/dl.

BRIEF DESCRIPTION OF DRAWINGS

FIGS. 1 to 4 show the following properties of xanthine oxidase of the present invention.

The ordinate shows relative activity (%), and the abscissa shows pH in FIGS. 1 and 2, and temperature °C. in FIGS. 3 and 4.

FIGS. 7–9 shows the relation between the optical density ($OD_{500}$) (ordinate) and the concentration of the substrate (mol) (abscissa) when the compounds mentioned below are subjected to an enzymatic reaction using the present enzyme.

FIG. 7: Hypoxanthine (1), Xanthine (2), Guanine (3)
FIG. 8: Inosine
FIG. 9: $KH_2PO_4$

BEST MODE OF CARRYING OUT THE INVENTION

Certain specific embodiments of the invention are illustrated by the following representative examples.

EXAMPLE 1

In this example, 10 ml of a seed medium comprising 0.5 g/dl yeast extract, 0.5 g/dl corn steep liquor, 0.1 g/dl peptone, 0.05 g/dl $KH_2PO_4$, 0.1 g/dl $K_2HPO_4$, 0.05 g/dl $MgSO_4.7H_2O$ and 0.35 g/dl guanosine (pH 7.2) are poured into 70 ml test tube and sterilized at 120° C. for 15 minutes. One loopful of *Enterobacter cloacae* KY 3066, FERM-P 4077, NRRL B-11155 is inoculated into the seed medium and cultured with shaking at 30° C. for 48 hours.

30 ml of the seed culture (the first seed culture) is transferred into 300 ml of a seed medium having the same composition as described above in a 2 l-Erlenmeyer flask and cultured with shaking at 30° C. for 48 hours. 900 ml of the thus obtained seed culture (the second seed culture) is transferred into 15 l of a medium having the same composition as described above in a 30 l-Jar fermenter and cultured at 30° C. for 40 hours with stirring at 300 r.p.m. and with aeration at 1 l/l/min. The resultant culture contains 0.31 U/ml of xanthine oxidase.

The recovery of xanthine oxidase from culture liquor is carried out as follows. The culture liquor is centrifuged to obtain 430 g of microbial cells (wet weight). The microbial cells are suspended in 2 l of 50 mM tris-hydrochloride buffer (pH 8.0) (the same buffer is used hereinafter) and the suspension is treated in a Dyno Laboratory Mill KDL type, (Willy A Bachofen Inc. Switzerland) for about 30 minutes to disrupt cells.

The resulting disrupted cell suspension is centrifuged to obtain about 3 l of supernatant.

To the supernatant, ammonium sulfate is added to 30% saturation and the formed precipitate is removed by centrifugation. The thus obtained supernatant is further mixed with ammonium sulfate to 55% saturation. The formed precipitate is recovered by centrifugation and dissolved in 100 ml of buffer. The resulting solution is dialyzed against 7 l of the same buffer using a cellophane tube as a dialysis membrane overnight. The solution in the dialysis tube is charged on a column packed with 1 l DEAE cellulose equilibrated in advance with buffer containing 0.2 M NaCl. After the column is washed with 2 l of the same buffer containing 0.2 M NaCl, concentration gradient elution is carried out with 4 l of the same buffer containing 0.2~0.6 M NaCl. The eluate is taken in 20 g fractions and the active fractions of xanthine oxidase are combined and mixed with ammonium sulfate to 65% saturation. The formed precipitate is recovered by centrifugation and is dissolved in the buffer. Then the resulting solution is charged on a column packed with 1 l of Sephadex G-150 and elution is carried out with the same buffer. The formed precipitate is dissolved in the buffer and the resulting solution is dialyzed against 3 l of the same buffer. Thereafter, the solution in the dialysis tube is charged on a column packed with 500 ml of DEAE-cellulose equilibrated in advance with the buffer containing 0.2 M NaCl. After the column is washed with 500 ml of the same buffer containing 0.2 M NaCl, concentration gradient elution is carried out with 2 l of the same buffer containing 0.2~0.6 M NaCl. The eluate is taken in 10 g fractions and the active fractions of xanthine oxidase are combined and mixed with ammonium sulfate to 65% saturation. The formed precipitate is recovered by centrifugation and dissolved in the buffer.

The resulting solution is dialyzed against 3 l of the same buffer. The solution in the dialysis tube is charged on a column packed with 500 ml of DEAE-Sephadex A-50 equilibrated in advance with the same buffer containing 0.25 M NaCl. After the column is washed with 1 l of the same buffer containing 0.25 M NaCl, concentration gradient elution is carried out with 2 l of the same buffer containing 0.25~0.6 M NaCl. The eluate is taken in 10 g fractions and the active fractions of xanthine oxidase are combined and dialyzed against 5 l of the same buffer. The resulting solution in the dialysis tube is freeze-dried, whereby 1.5 g of a powder of xanthine oxidase is obtained.

The yield in terms of activity based on the supernatant obtained by centrifuging the disrupted cell suspension is 12.5%. The specific activity of the powder is 7.5 U/mg of protein.

EXAMPLE 2

In this example, 40 ml of the medium (pH 7.2) containing 0.5 g/dl yeast extract, 0.5 g/dl corn steep liquor, 0.1 g/dl peptone, 0.05 g/dl $KH_2PO_4$, 0.1 g/dl $K_2HPO_4$, 0.05 g/dl $MgSO_4.7H_2O$ and 0.27 g/dl hypoxanthine is poured into Sakaguchi-flask and is sterilized at 120° C. for 15 minutes. One loopful of the seed culture of *Enterobacter cloacae* KY 3066 is inoculated into the medium and culturing is carried out at 30° C. for 48 hours.

The microbial cells are recovered from the culture liquor by centrifugation and are suspended in 20 ml of the buffer. The suspension is subjected to ultrasonic disintegration. The resulting disrupted cell suspension is centrifuged to obtain a supernatant which exhibits xanthine oxidase activity of 0.31 U/ml of culture liquor.

EXAMPLE 3

The same procedures as described in Example 2 are repeated except that the compounds shown in Table 5 are used instead of hypoxanthine, whereby the results shown in Table 5 are obtained.

TABLE 5

| Compound added | Amount of addition (g/dl) | Xanthine oxidase (U/ml) |
|---|---|---|
| Xanthine | 0.3 | 0.13 |
| Guanine | 0.3 | 0.14 |
| Inosine | 0.54 | 0.20 |
| Xanthosine | 0.57 | 0.20 |
| Disodium 2,5'-inosinate | 0.78 | 0.15 |
| Disodium 2,5'-guaninate | 0.81 | 0.30 |

EXAMPLE 4

Figure 7:
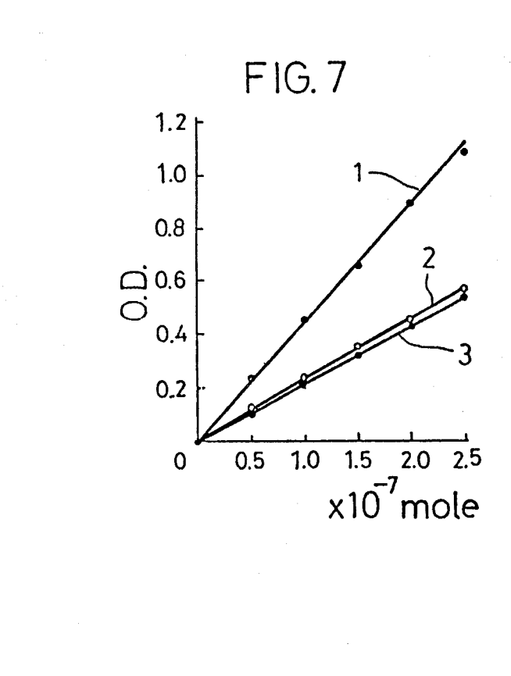

In this example, 1.2 ml of 0.1 M tris-hydrochloride buffer (pH 7.3), 0.2 ml of coloring solution and 2 U of xanthine oxidase are added to 0.1 ml of solution containing hypoxanthine, xanthine or guanine as the substrate in a concentration indicated in FIG. 7 and the mixture is made up to 3 ml with water.

As the coloring solution, 0.1 M tris-hydrochloride buffer (pH 7.3) containing 10 mmol/l 4-aminoantipyrine, 10 mmol/l phenol and 9.8 U/ml peroxidase is used. The resultant mixture is subjected to reaction at 37° C. for 15 minutes and the absorbancy of the reaction solution is measured at 500 nm. The results are shown in FIG. 7.

EXAMPLE 5

Figure 8:
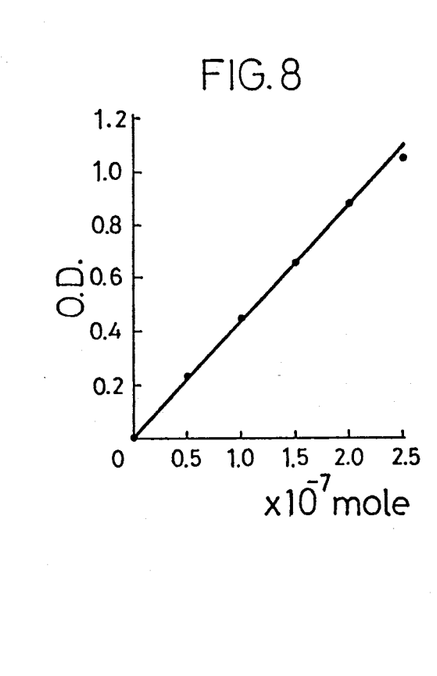

In this example, 1.0 ml of 1/15 M phosphate buffer (pH 7.3), 0.2 ml of coloring solution of Example 4, 1 U of purine nucleoside phosphorylase, and 5 U of xanthine oxidase are added to 0.1 ml of inosine solution having a concentration indicated in FIG. 8 and the mixture is made up to 3 ml with water.

The mixture is subjected to reaction under the same reaction condition as described in Example 4 and the absorbancy of the reaction solution is measured at 500 nm. The results are shown in FIG. 8.

EXAMPLE 6

Figure 9:
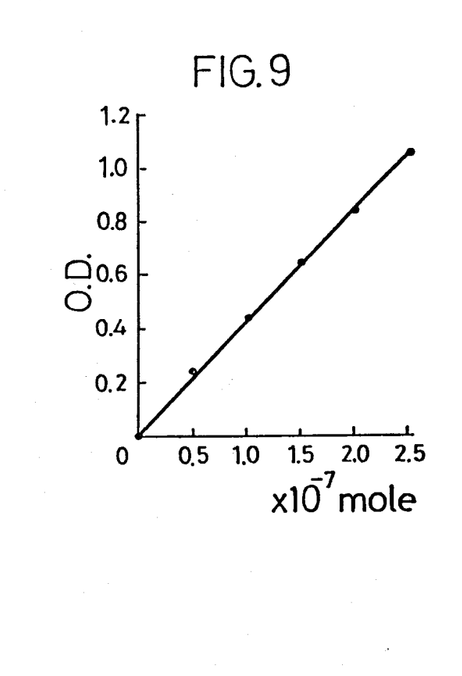

In this example, 0.2 ml of coloring solution of Example 4, 0.2 ml of 10 mM inosine solution, 1 U of purine nucleoside phosphorylase, 5 U of xanthine oxidase and 0.1 ml of $KH_2PO_4$ solution having a concentration indicated in FIG. 9 are added to 1.0 ml of 0.1 M tris-hydrochloride buffer (pH 7.3) and the mixture is made up to 3 ml with water. The mixture is subjected to reaction under the same reaction condition as in Example 4 and the absorbancy of the reaction solution is measured at 500 nm. The results are shown in FIG. 9.

We claim:

1. Xanthine oxidase having the following enzymological properties:
   (1) Staple pH range: 6.2–6.8
   (2) Optimum pH: about 7.1
   (3) Optimum temperature: 35°–45° C.
   (4) Molecular weight: 128,000
   (5) Best acceptor of the enzyme: oxygen.

2. A method for the determination of the substrate for xanthine oxidase which comprises oxidizing the substrate in a sample by the action of the xanthine oxidase of claim 1 to form hydrogen peroxide, reacting the formed hydrogen peroxide with a coloring reagent in the presence of peroxidase and measuring the absorbency of the reaction solution in the visible ray region.

3. A method according to claim 1 wherein said substrate is at least one member selected from the group consisting of xanthine, hypoxanthine, 2-hydroxypurine and guanine.

4. A method according to claim 1 wherein said coloring reagent comprises 4-aminoantipyrine and phenol.

5. A method according to claim 1 wherein said substrate for xanthine oxidase is a product of a reaction or decomposition.

6. A method according to claim 5 wherein said reaction is an enzymatic reaction.

7. A method according to claim 1 wherein said substrate is a product derived from purine base or phosphoric acid.

8. A method according to claim 7 wherein said purine base is inosine, xanthosine, guanosine, adenosine, adenine or deoxyinosine.

9. A test composition for the determination of the substrate for xanthine oxidase which comprises xanthine oxidase as defined in claim 1 and a system comprising peroxidase and a coloring reagent for determining the amount of hydrogen peroxide.

10. A test composition according to claim 9 wherein said substrate is at least one member selected from the group consisting of xanthine, hypoxanthine, 2-hydroxypurine and guanine.

11. A test composition according to claim 9 wherein said coloring reagent comprises 4-aminoantipyrine and phenol.

12. A test composition for the determination of purine base which comprises purine nucleoside phosphorylase and a test composition according to claim 9.

13. A test composition according to claim 12 wherein said purine base is inosine, xanthosine, guanosine, adenosine, adenine or deoxyinosine.

14. A test composition for the determination of phosphoric acid which comprises purine base, purine nucleoside phosphorylase and a test composition according to claim 9.

15. A process for producing xanthine oxidase which comprises culturing a microorganism belonging to the genus Enterobacter and capable of producing xanthine oxidase in a nutrient medium, forming xanthine oxidase in the culture liquor and recovering the same therefrom.

16. A process according to claim 5 wherein said microorganism belongs to the species *Enterobacter cloacae*.

17. A process according to claim 15 wherein said microorganism is *Enterobacter cloacae* KY 3066, NRRL B-11155.

* * * * *